United States Patent
Coulomb et al.

(10) Patent No.: US 11,859,151 B2
(45) Date of Patent: Jan. 2, 2024

(54) CYCLOPENTANONE COMPOUNDS

(71) Applicant: FIRMENICH SA, Satigny (CH)

(72) Inventors: Julien Coulomb, Satigny (CH); Edouard Demole, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 15/734,687

(22) PCT Filed: Oct. 14, 2019

(86) PCT No.: PCT/EP2019/077756
§ 371 (c)(1),
(2) Date: Dec. 3, 2020

(87) PCT Pub. No.: WO2020/078892
PCT Pub. Date: Apr. 23, 2020

(65) Prior Publication Data
US 2021/0230503 A1  Jul. 29, 2021

(30) Foreign Application Priority Data

Oct. 15, 2018  (EP) ..................................... 18200512

(51) Int. Cl.
| | | |
|---|---|---|
| C11B 9/00 | (2006.01) | |
| A61K 8/35 | (2006.01) | |
| C11D 3/00 | (2006.01) | |
| C11D 3/20 | (2006.01) | |
| C11D 3/50 | (2006.01) | |
| A61Q 1/00 | (2006.01) | |
| A61Q 3/00 | (2006.01) | |
| A61Q 5/02 | (2006.01) | |
| A61Q 5/06 | (2006.01) | |
| A61Q 5/10 | (2006.01) | |
| A61Q 9/02 | (2006.01) | |
| A61Q 9/04 | (2006.01) | |
| A61Q 11/00 | (2006.01) | |
| A61Q 15/00 | (2006.01) | |
| A61Q 19/00 | (2006.01) | |
| A61Q 19/04 | (2006.01) | |
| A61Q 19/10 | (2006.01) | |
| C11D 11/00 | (2006.01) | |

(52) U.S. Cl.
CPC ................ *C11B 9/003* (2013.01); *A61K 8/35* (2013.01); *A61Q 1/00* (2013.01); *A61Q 3/00* (2013.01); *A61Q 5/02* (2013.01); *A61Q 5/06* (2013.01); *A61Q 5/10* (2013.01); *A61Q 9/02* (2013.01); *A61Q 9/04* (2013.01); *A61Q 11/00* (2013.01); *A61Q 15/00* (2013.01); *A61Q 19/002* (2013.01); *A61Q 19/04* (2013.01); *A61Q 19/10* (2013.01); *C11D 3/0015* (2013.01); *C11D 3/2072* (2013.01); *C11D 3/50* (2013.01); *C11D 11/0017* (2013.01)

(58) Field of Classification Search
CPC ........... A23L 27/203; A61K 8/35; A61Q 1/00; A61Q 3/00; A61Q 5/02; A61Q 5/06; A61Q 5/10; A61Q 9/02; A61Q 9/04; A61Q 11/00; A61Q 15/00; A61Q 19/002; A61Q 19/04; A61Q 19/10; C07C 49/647; C07C 2601/08; C11B 9/003; C11D 3/0015; C11D 3/2072; C11D 3/50; C11D 11/0017

See application file for complete search history.

(56) References Cited

U.S. PATENT DOCUMENTS

| | | |
|---|---|---|
| 4,217,251 A | 8/1980 | Dastur |
| 5,283,237 A | 2/1994 | Boden et al. |
| 2008/0125345 A1 | 5/2008 | Zucca et al. |

OTHER PUBLICATIONS

D. Belsito et al. (2012) A toxicologic and dermatologic assessment of cyclopentanones and cyclopentenones when used as fragrance ingredients, Food and Chemical Toxicology, 50:3, S517-S556, DOI:10.1016/j.fct.2012.04.019 (Year: 2012).*
D. Belsito et al. (2012) A toxicologic and dermatologic assessment of cyclopentanones and cyclopentenones when used as fragrance ingredients, Food and Chemical Toxicology, 50:3, $517-S556, DOI:10.1016/).fct.2012.04.019 (Year: 2012).*
B. Westermann & I. Kortmann (1994), Biocatalysis, 10:1-4, 289-294 (Year: 1994).*
International Search Report and Written Opinion for corresponding PCT/EP2019/077756 dated Nov. 20, 2019, 15 pages.
G. Mandville, F. Leyendecker, J.- M. Conia, "N° 155.—Thermolyse et photolyse de cétones non saturées. XXI-La synthèse de cétones spiraniques par thermocyclisation d'alcenyl-2- et d'alcynyl-2-cyclopentanones et-cyclohexanones.", Bulletin De La Societe Chimique De France, 1973, p. 963-971.
Wright J, "(E)-2-(3,7-Dimethyl 2,6-octadienyl) cyclopentanone.", PERFUMER & FLAVORIST 2016 E-MAIL JOHNWRIGHTFLAVORIST@GMAIL.COM,vol. 41, No. 6, Jun. 2016 (Jun. 2016), p. 20, 22.
Yamamoto T et al, "Synthesis and odor of optically active 2-n-hexyl- and 2-n-heptylcyclopentanone and the corresponding @d-lactones", Dec. 9, 2002 (Dec. 9, 2002), vol. 43, No. 50, p. 9081-9084.

(Continued)

*Primary Examiner* — Adam C Milligan
*Assistant Examiner* — Amanda Michelle Petritsch
(74) *Attorney, Agent, or Firm* — Armstrong Teasdale LLP

(57) ABSTRACT

Described herein is a method of using as perfuming ingredients, e.g. to impart odor notes of the fruity, fruity-exotic types, cyclopentanone compounds of formula

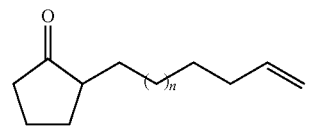

(I)

in a form of any one of its stereoisomers or a mixture thereof, and wherein n represents 1 or 2.

1 Claim, No Drawings

(56) References Cited

OTHER PUBLICATIONS

Nokami J. et al. "Intramolecular Allylation Of Carbonyl Compounds—A New Method for Five and Six Membered Ring Formation" Chemistry Letters (1984) pp. 869-870.
Westermann B., et al. "Preparation of Optically Active ß-Ketoesters via PLE-catalyzed Resolution" Biocatalysis (1994) vol. 10 pp. 289-294.
Winkler, J. D. et al. "Inside-Outside Stereoisomerism" Americal Chemical Society, vol. 116, No. 10, (1994) pp. 4183-4188.
Molander, G. A. et al. "Synthesis of Substituted Cyclooctanols by a Samarium (II) Iodide Promoted 8-Endo Radical Cyclization Process" J. Org. Chem., vol. 59, No. 11 (1994) pp. 3186-3192.

\* cited by examiner

CYCLOPENTANONE COMPOUNDS

CROSS-REFERENCE TO RELATED APPLICATIONS

This application is a U.S. National Phase Application of International Patent Application No. PCT/EP2019/077756, filed October 14, 2019. which claims the benefit of priority to European Patent Application No. 18200512.4. filed October 15. 2018, the entire contents of which are hereby incorporated by reference herein.

TECHNICAL FIELD

The present invention relates to the field of perfumery. More particularly, it concerns the use as perfuming ingredients of cyclopentanone compounds. The present invention concerns the use of said compounds in the perfumery industry as well as the compositions or articles containing said compounds.

Background of the Invention

To the best of our knowledge, none of the invention's compounds is known as perfuming compound or as having an odor in general.

Some of the invention's compounds may be known per se but would have been cited only as chemical intermediates such as in J. Am. Chem. Soc., 1994, 116, 4183-4188, J. Org. Chem., 1994, 59, 3186-3192, Biocatalysis, 1994, 10, 289-294 or Chemistry Letters, 1984, 869-870.

However, these prior art documents do not report or suggest any organoleptic properties of the compounds of formula (I), or any use of said compounds in the field of perfumery.

SUMMARY OF THE INVENTION

The invention relates to compound of formula (I) imparting fruity-exotic notes and devoided of floral aspect.

So, a first object of the present invention is the use as perfuming ingredient of a compound of formula

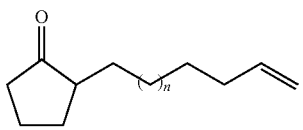

(I)

in the form of any one of its stereoisomers or a mixture thereof, and wherein n represents 1 or 2.

The second object of the present invention is a Method to confer, enhance, improve or modify the odor properties of a perfuming composition or of a perfumed article, which method comprises adding to said composition or article an effective amount of at least a compound of formula

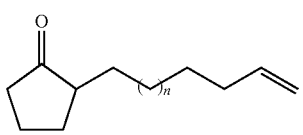

(I)

in the form of any one of its stereoisomers or a mixture thereof, and wherein n represents 1 or 2.

The third object of the present invention is a perfuming composition comprising i) at least one compound of formula (I), as defined above;
ii) at least one ingredient selected from the group consisting of a perfumery carrier and a perfumery base; and
iii) optionally at least one perfumery adjuvant.

Another object of the present invention is a perfumed consumer product comprising at least one compound of formula (I) as defined above or a composition as defined above.

Description of the invention

Surprisingly, it has now been discovered that a compound of formula

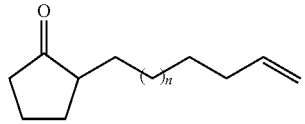

(I)

in the form of any one of its stereoisomers or a mixture thereof, and wherein n represents 1 or 2, can be used as perfuming ingredient, for instance to impart odor notes of the fruity, fruity-exotic types.

For the sake of clarity, by the expression "any one of its stereoisomers or as a mixture thereof", or the similar, it is meant the normal meaning understood by a person skilled in the art, i.e. that the invention compound can be a pure enantiomer or be in the form of a mixture of enantiomers.

According to a particular embodiment of the invention, n represents 1.

According to a particular embodiment of the invention, the compound of formula (I) is 2-(hex-5-en-1-yl)cyclopentan-1-one.

As specific examples of the invention's compounds, one may cite, as non-limiting example, 2-(hex-5-en-1-yl)cyclopentan-1-one, which possesses a fruity-lactonic-exotic, mango and passionfruit like olfactive connotation.

When the odor of the invention's compounds is compared with that of the prior art compound 2-pentylcyclopentan-1-one, then the invention's compounds distinguish themselves by a clearly stronger fruity-exotic note and by lacking the floral-jasmonic note so characteristic of the prior art compound.

Said differences lend the invention's compounds and the prior art compound to be each suitable for different uses, i.e. to impart different organoleptic impressions.

As mentioned above, the invention concerns the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol" (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. Solid carriers areof current use in the art and a person skilled in the art knows how to reach the desired effect. However by way of non-limiting examples of solid carriers, one may cite absorbing gums or polymers or inorganic materials, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- und Geliermittel in Lebensmitteln, Band 2 der Schriftenreihe Lebensmittelchemie, Lebensmittelqualittt, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation techniques.

As non-limiting examples of solid carriers, one may cite in particular the core-shell capsules with resins of aminoplast, polyamide, polyester, polyurea or polyurethane type or a mixture threof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Other resins are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate*, origin: Mitsui Chemicals), among which a trimer of xylylene diisocyanate with trimethylolpropane and a Biuret of hexamethylene diisocyanate are preferred.

Some of the seminal literature related to the encapsulation of perfumes by polycondensation of amino resins, namely melamine based resins with aldehydes includes articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. US 4'396'670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of K. Bruyninckx and M. Dusselier, ACS Sustainable Chemistry & Engineering, 2019, vol. 7, pages 8041-8054.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin.

In particular one may cite perfuming co-ingredients knows for having a similar olfactive note, such as:

In particular one may cite perfuming co-ingredients which are commonly used in perfume formulations, such as:

Aldehydic ingredients: decanal, dodecanal, 2-methyl-undecanal, 10-undecenal, octanal, nonanal and/or nonenal;

Aromatic-herbal ingredients: *eucalyptus* oil, camphor, eucalyptol, 5-methyltricyclo[6.2.1.0-2,7-]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients:methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-11S)-1-[(1R)-3,3-dimethylcyclohexyl]ethoxy]-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-oneand/or (1S,1'R)-[1-(3',3'-dimethyl-1'-cyclohexyl)ethoxycarbonyl]methyl propanoate, ;

Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2'7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, clearwood*, (1'R, E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds also known as properfume or profragrance. Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate or a mixture thereof.

By "perfumery adjuvant", it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of by a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer products include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc..); or a home care product, such as a mold remover, a furniture care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer product, typical concentrations are in the order of 0.001% to 5% by weight, or even more, of the compounds of the invention based on the weight of the consumer product into which they are incorporated.

The invention's compounds can be prepared according to standard method known in the art as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of compounds of formula (I)

2-(hex-5-en-1-yl)cyclopentan-1-one

Step 1: ethyl 1-(hex-5-en-1-yl)-2-oxocyclopentane-1-carboxylate:

To a solution of ethyl 2-oxocyclopentane-1-carboxylate (56 mL, 375 mmol, 1 equiv.) in acetone (871 mL) at r.t. was rapidly added potassium carbonate (118 g, 845 mmol, 2.25 equiv.) and potassium iodide (20 g, 120 mmol, 0.32 equiv.).

After stirring for 10 min, a solution of 6-bromohex-1-ene (51 mL, 381 mmol, 1.01 equiv.) in acetone (232 ml) was added and the reaction was refluxed for 19 h. Diethyl ether (900 mL) was added, the mixture was filtered on a Celite pad and the solvent was evaporated. The residue was diluted with ether, washed with water and brine, dried over sodium sulfate, filtered and concentrated in vacuo to afford ethyl 1-(hex-5-en-1-yl)-2-oxocyclopentane-1-carboxylate as an oil (93.3 g, 91% purity, 95% yield).

$^1$H NMR: 1.25 (t, J=7.1 Hz, 3H), 1.27-1.42 (m, 4H), 1.53-1.59 (m, 1H), 1.86-2.07 (m, 6H), 2.21-2.28 (m, 1H), 2.37-2.44 (m, 1H), 2.50-2.56 (m, 1H), 4.11-4.21 (m, 2H), 4.92-5.01 (m, 2H), 5.73-5.82 (m, 1H).

$^{13}$C NMR: 215.0 (s), 171.1 (s), 138.6 (d), 114.5 (t), 61.3 (t), 60.5 (s), 38.0 (t), 33.7 (t), 33.4 (t), 32.7 (t), 29.1 (t), 24.3 (t), 19.6 (t), 14.1 (q).

Step 2: 2-(hex-5-en-)-yl)cyclopentan-1-one:

To a solution of the keto-ester of step 1 (93.3 g, 91% purity, 356 mmol, 1 equiv.) in methanol (860 mL) at r.t. was added a 6 M aqueous HCl solution (428 mL, 2.57 mol, 7.2 equiv.) dropwise. The reaction was refluxed for 6 days. Diethyl ether was added and the aqueous layer was extracted with ether twice. The combined organic extracts were washed sequentially with water, a saturated solution of sodium bicarbonate, water and brine, dried over sodium sulfate, filtered and concentrated in vacuo. The residue was purified by distillation on a Vigreux column (92-93° C., 1.5 mbar) to afford the desired ketone as an oil (42.0 g, 71% yield).

$^1$H NMR: 1.21-1.44 (m, 5H), 1.46-1.56 (m, 1H), 1.71-1.83 (m, 2H), 1.96-2.15 (m, 5H), 2.18-2.33 (m, 2H), 4.91-5.02 (m, 2H), 5.74-5.85 (m, 1H).

$^{13}$C NMR: 221.5 (s), 138.9 (d), 114.4 (t), 49.1 (d), 38.2 (t), 33.6 (t), 29.6 (t), 29.5 (t), 28.9 (t), 27.0 (t), 20.8 (t).

2-(hept-6-en-1-yl)cyclopentan-1-one

Step 1: ethyl 1-(hept-6-en-1-yl)-2-oxocyclopentane-1-carboxylate:

To a solution of ethyl 2-oxocyclopentane-1-carboxylate (3.56 mL, 26.7 mmol, 1 equiv.) in acetone (62 mL) at r.t. was rapidly added potassium carbonate (8.43 g, 60.4 mmol, 2.25 equiv.) and potassium iodide (1.43 g, 8.55 mmol, 0.32 equiv.). After stirring for 10 min, a solution of 7-bromohept-1-ene (4.23 mL, 26.9 mmol, 1.01 equiv.) in acetone (17 ml) was added and the reaction was refluxed for 23 h. Diethyl ether (100 mL) was added, the mixture was filtered on a Celite pad and the solvent was evaporated. The residue was diluted with ether, washed with water and brine, dried over sodium sulfate, filtered and concentrated in vacuo to afford ethyl 1-(hept-6-en-1-yl)-2-oxocyclopentane-1-carboxylate as an oil (6.37 g, 88% purity, 92% yield).

Step 2: 2-(hept-6-en-1-yl)cyclopentan-1-one:

To a solution of the keto-ester of step 1 (6.64 g, 88% purity, 24.5 mmol, 1 equiv.) in methanol (59 mL) at r.t. was added a 6 M aqueous HCl solution (29.4 mL, 177 mol, 7.2 equiv.) dropwise. The reaction was refluxed for 5 days. Diethyl ether was added and the aqueous layer was extracted with ether twice. The combined organic extracts were washed sequentially with water, a saturated solution of sodium bicarbonate, water and brine, dried over sodium sulfate, filtered and concentrated in vacuo. The residue was purified by flash column chromatography on silica gel (Heptane/AcOEt 95:5) and bulb-to-bulb distillation (115° C., 0.8-0.9 mbar) to afford the desired ketone as an oil (3.06 g, 68 % yield).

$^1$H NMR (CDCl$_3$, 400 MHz): 1.22-1.41 (m, 7H), 1.48-1.55 (m, 1H), 1.73-1.81 (m, 2H), 1.97-2.13 (m, 5H), 2.19-2.23 (s, 1H), 2.27-2.31 (m, 1H), 4.95-5.00 (m, 2H), 5.76-5.83 (m, 1H).

$^{13}$C NMR (CDCl$_3$, 100 MHz): 221.6 (s), 139.0 (d), 114.3 (t), 49.1 (d), 38.2 (t), 33.7 (t), 29.7 (t), 29.6 (t), 29.1 (t), 28.7 (t), 27.4 (t), 20.8 (t).

Example 2

Preparation of a Perfuming Composition

A perfuming composition was prepared by admixing the following ingredients:

| Ingredient | Parts by weight |
| --- | --- |
| Amyl acetate | 40 |
| Ethyl acetate | 20 |
| Hexyl acetate | 200 |
| Isobutyl acetate | 60 |
| Benzyl acetate | 80 |
| Geranyl acetate | 160 |
| Linalyl acetate | 400 |
| (Z)-3-hexen-1-ol acetate | 60 |
| Styrallyl acetate | 80 |
| 10%* Methylbutyric acid | 40 |
| Benzoic aldehyde | 40 |
| 10%* methyl anthranilate | 40 |
| Carbinol butyrate | 80 |
| (Z)-3-hexen-1-ol butyrate | 20 |
| Ethyl caproate | 40 |
| Hexyl caproate | 80 |
| (Z)-3-hexen-1-ol caproate | 20 |
| Lemon | 160 |
| Maltol | 80 |
| 10%* Damascenon | 40 |
| γ-n-decalactone | 800 |
| 1%* Dimethylsulfid | 40 |
| Dodecalactone | 800 |
| Ethylvanillin | 100 |
| 3-(4-Methoxyphenyl)-2-methylpropanal | 80 |
| Gamma hexalactone | 40 |
| Gamma jasmolactone | 10 |
| Gamma nonalactone | 40 |
| Gamma undecalactone | 600 |
| Geraniol | 400 |
| Habanolide ®[1] | 800 |
| Hedione ®[2] | 300 |
| Helvetolide ®[3] | 80 |
| Ethyl isobutyrate | 40 |
| Limonene | 160 |
| Linalol | 1600 |
| Menthol | 10 |
| 10%* Methylisopropylthiazol | 20 |
| Ocimene | 40 |
| 10%* Orange aldehyde | 80 |
| 1%*, (3Z)-1-(2-butenyloxy)-3-Hexene | 80 |
| Linalyl ether | 80 |
| 10%* (2E,6Z)-2,6-nonadienal | 40 |
| (Z)-3-hexen-1-ol dist | 160 |
| Hexyl salicylate | 800 |
| (Z)-3-hexen-1-ol salicylate | 100 |
| Terpineol | 600 |
| Verdox[4] | 80 |
| Beta ionone | 200 |
| | 9920 |

*in dipropyleneglycol
[1]pentadecenolide; origin: Firmenich SA, Geneva, Switzerland
[2]Methyl dihydrojasmonate; origin: Firmenich SA, Geneva, Switzerland
[3](1S,1'R)-2-[1-(3',3'-dimethyl-1'-cyclohexyl)ethoxy]-2-methylpropyl propanoate; origin: Firmenich SA, Geneva, Switzerland
[4]2-tert-butyl-1-cyclohexyl acetate; origin: International Flavors & Fragrances, USA The addition of 80 parts by weight of 2-(hex-5-en-1-yl) cyclopentan-1-one to the above-described composition imparted to the latter a fruity-exotic (mango and passionfruit like) connotation with a slightly acidulous facet which makes the fragrance more juicy and natural.

When, instead of the invention's compound, 2-heptylcyclopentan-1-one (Fleuramone) was added, there is little effect observed in the above-described composition. The above-described composition becomes just slightly more floral (jasmine like).

When, instead of the invention's compound, 2-pentylcyclopentan-1-one (Delphone) was added, the perfumery composition becomes much greener (celery like) and more floral (jasmine like).

Example 3

Preparation of a Liquid Detergent Comprising the Invention's Compound

TABLE 1

Composition of the liquid detergent formulation

| Ingredients | Concentration [wt %] |
|---|---|
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Properase L[4] | 0.2 |
| Puradax EG L[4] | 0.2 |
| Purastar ST L[4] | 0.2 |
| Acrylates/Steareth-20 Methacrylate structuring Crosspolymer[5] | 6 |
| Deionized Water | 27.4 |

[1] Hostapur SAS 60; Origin: Clariant
[2] Edenor K 12-18; Origin: Cognis
[3] Genapol LA 070; Origin: Clariant
[4] Origin: Genencor International
[5] Aculyn 88; Origin: Dow Chemical The liquid detergent was prepared by adding 1.5% by weight, relative to the total weight of the liquid detergent, of the invention's composition of example 2 into the unperfumed liquid detergent formulation of Table 1 under gentle shaking.

Example 4

Preparation of a Fabric Softener Comprising the Invention's Compound

TABLE 2

Composition of the softener formulation

| Ingredient | Concentration [wt %] |
|---|---|
| Methyl bis[ethyl (tallowate)]-2-hydroxyethyl ammonium methyl sulfate[1] | 12.20 |
| 1,2-benzisothiazolin-3-one[2] | 0.04 |
| CaCl$_2$ (10% aqueous solution) | 0.40 |
| Water | 87.36 |

[1] Stepantex VL90 A Diester Quat; Origin: Stepan
[2] Proxel GXL; Origin: Arch

The softener was prepared by weighting Methyl bis[ethyl (tallowate)]-2-hydroxyethyl ammonium methyl sulfate which was heated at 65° C. Then Water and 1,2-benzisothiazolin-3-one were placed in the reactor and were heated at 65° C. under stirring. To the above mixture was added Methyl bis[ethyl (tallowate)]-2-hydroxyethyl ammonium methyl sulfate. The mixture was stirred 15 minuted and CaCl$_2$ was added. Then 0.5 to 2% by weight, relative to the total weight of the softener, of the invention's composition of example 2 was added. The mixture was stirred 15 minutes and was cooled down to room temperature under stirring (viscosity measure: result 35+/−5 mPas. (shear rate 106 sec-1)).

Example 5

Preparation of a Transparent Isotropic Shampoo Comprising the Invention's Composition

TABLE 3

Composition of the transparent isotropic shampoo formulation

| Phases | Ingredients | Concentration [wt %] |
|---|---|---|
| A | Water deionized | 44.4 |
|   | Polyquaternium-10[1] | 0.3 |
|   | Glycerin 85%[2] | 1 |
|   | DMDM Hydantoin[3] | 0.2 |
| B | Sodium Laureth Sulfate[4] | 28 |
|   | Cocamidopropyl Betaine[5] | 3.2 |
|   | Disodium Cocoamphodiacetate[6] | 4 |
|   | Ethoxy (20) Stearyl Alcohol[6] | 1 |
| C | Sodium Laureth Sulfate[4] | 3 |
|   | Glyceryl Laureate[7] | 0.2 |
| D | Water deionized | 1 |
|   | Sodium Methylparaben[8] | 0.1 |
| E | Sodium Chloride 10% aqueous sol. | 15 |
|   | Citric acid 10% aqueous sol. till pH 5.5-6 | q.s. |

[1] Ucare Polymer JR-400, Origin: Noveon
[2] Origin: Schweizerhall
[3] Glydant, Origin: Lonza
[4] Texapon NSO IS, Origin: Cognis
[5] Tego Betain F 50, Origin: Evonik
[6] Amphotensid GB 2009, Origin: Zschimmer & Schwarz
[7] Monomuls 90 L-12, Origin: Gruenau
[8] Nipagin Monosodium, Origin: NIPA The shampoo was prepared by dispersed in water Polyquaternium-10. The remaining ingredients of phase A were mixed separately by addition of one after the other while mixing well after each adjunction. This pre-mix was added to the Polyquaternium-10 dispersion and mixed for another 5 min. Then, the premixed phase B and the premixed Phase C were added (Monomuls 90L-12 was heated to melt in Texapon NSO IS) while agitating. Phase D and Phase E were added while agitating. PH was adjusted with citric acid solution till pH: 5.5-6.0 leading to an unperfumed shampoo formulae.

The perfumed shampoo was prepared by adding 0.4 to 0.8% by weight, relative to the total weight of the shampoo, of the invention's composition of example 2 into the unperfumed shampoo formulation of Table 3 under gentle shaking.

Example 6

Preparation of a Structured Shower Gel Comprising the Invention's Composition

TABLE 4

| Composition of the shower gel formulation | |
|---|---|
| Ingredients | Amount (% wt) |
| WATER deionised | 49.350 |
| Tetrasodium EDTA[1] | 0.050 |
| Acrylates Copolymer[2] | 6.000 |
| Sodium C12-C15 Pareth Sulfate[3] | 35.000 |
| Sodium Hydroxide 20% aqueous solution | 1.000 |
| Cocamidopropyl Betaine[4] | 8.000 |
| Methylchloroisothiazolinone and Methylisothiazolinone[5] | 0.100 |
| Citric Acid (40%) | 0.500 |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS The shower gel was prepared by adding 0.5 to 1.5% by weight, relative to the total weight of the shower gel, of the invention's composition of example 2 into the unperfumed shower gel formulation of Table 4 under gentle shaking.

Example 7

Preparation of a Transparent Shower Gel Comprising the Invention's Composition

TABLE 5

| Composition of the transparent shower gel formulation | |
|---|---|
| Ingredients | Concentration (% wt) |
| WATER deionized | 52.40 |
| Tetrasodium EDTA[1] | 0.10 |
| Sodium Benzoate | 0.50 |
| Propylene Glycol | 2.00 |
| Sodium C12-C15 Pareth Sulfate[2] | 35.00 |
| Cocamidopropyl Betaine[3] | 8.00 |
| Polyquaternium-7[4] | 0.20 |
| Citric Acid (40%) | 1.00 |
| Sodium Chloride | 0.80 |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL The transparent shower gel was prepared by adding 0.5 to 1.5% by weight, relative to the total weight of the shower gel, of the invention's composition of example 2 into the unperfumed shower gel formulation of Table 5 under gentle shaking.

Example 8

Preparation of a Milky Shower Gel Comprising the Invention's Composition

TABLE 6

| Composition of the milky shower gel formulation | |
|---|---|
| Ingredients | Concentration (% wt) |
| WATER deionized | 50.950 |
| Tetrasodium EDTA[1] | 0.050 |
| Sodium Benzoate | 0.500 |
| Glycerin 86% | 3.500 |
| Sodium Laureth Sulfate[2] | 27.000 |
| Polyquaternium-7[3] | 1.000 |
| Coco-Betaine[4] | 6.000 |
| PEG-120 Methyl Glucose trioleate[5] | 1.000 |
| Citric Acid (40%) | 1.000 |
| Glycol Distearate & Laureth-4 & Cocamidopropyl Betaine[6] | 3.000 |
| Sodium Chloride 20% | 5.000 |
| PEG-40 Hydrogenated Castor Oil[7] | 1.000 |

[1] EDETA B POWDER; trademark and origin: BASF
[2] Texapon NSO IS; trademark and origin: COGNIS
[3] MERQUAT 550; trademark and origin: LUBRIZOL
[4] DEHYTON AB-30; trademark and origin: COGNIS
[5] GLUCAMATE LT; trademark and origin: LUBRIZOL
[6] EUPERLAN PK 3000 AM; trademark and origin: COGNIS
[7] CREMOPHOR RH 40; trademark and origin: BASF The transparent shower gel was prepared by adding 0.5 to 1.5% by weight, relative to the total weight of the shower gel, of the invention's composition of example 2 into the unperfumed shower gel formulation of Table 6 under gentle shaking.

Example 9

Preparation of a Pearly Shampoo Comprising the Invention's Composition

TABLE 7

| Phases | Ingredients | Concentration (% wt) |
|---|---|---|
| A | Water deionized | 45.97 |
| | Tetrasodium EDTA[1] | 0.05 |
| | Guar Hydroxypropyltrimonium Chloride[2] | 0.05 |
| | Polyquaternium-10[3] | 0.075 |
| B | NaOH 10% aqueous sol. | 0.3 |
| C | Ammonium Lauryl Sulfate[4] | 34 |
| | Ammonium Laureth Sulfate[5] | 9.25 |
| | Cocamidopropyl Betaine[6] | 2 |
| | Dimethicone (&) C12-13 Pareth-4 (&) C12-13 Pareth-23 (&) Salicylic Acid[7] | 2.5 |
| D | Cetyl Alcohol[8] | 1.2 |
| | Cocamide MEA[9] | 1.5 |
| | Glycol Distearate[10] | 2 |

TABLE 7-continued

Composition of the pearly isotropic shampoo formulation

| Phases | Ingredients | Concentration (% wt) |
|---|---|---|
| E | Methylchloroisothiazolinone & Methylisothiazolinone[11] | 0.1 |
|  | D-Panthenol 75%[12] | 0.1 |
|  | Water deionized | 0.3 |
| F | Sodium Chloride 25% aqueous sol. | 0.6 |

[1]EDETA B Powder, Origin: BASF
[2]Jaguar C14 S, Origin: Rhodia
[3]Ucare Polymer JR-400, Origin: Noveon
[4]Sulfetal LA B-E, Origin: Zschimmer & Schwarz
[5]Zetesol LA, Origin: Zschimmer & Schwarz
[6]Tego Betain F 50, Origin: Evonik
[7]Xiameter MEM-1691, Origin: Dow Corning
[8]Lanette 16, Origin: BASF
[9]Comperlan 100, Origin: Cognis
[10]Cutina AGS, Origin: Cognis
11)Kathon CG, Origin: Rohm & Haas
12)D-Panthenol, Origin: Roche The shampoo was prepared by dispersed in water and Tetrasodium EDTA, Guar Hydroxypropyltrimonium Chloride and Polyquaternium-10. NaOH 10% solution (Phase B) was added once Phase A was homogeneous. Then, the premixed Phase C was added, and mixture was heated to 75° C. Phase D ingredients were added and mixed till homogeneous. The mixture was cooled down. At 45° C., Phase E ingredients were added while mixing. Final viscosity was adjusted with 25% NaCl solution and pH of 5.5-6 was adjusted with 10% NaOH solution.

The perfumed pearly shampoo was prepared by adding 0.4 to 0.8% by weight, relative to the total weight of the shampoo, of the invention's composition of example 2 into the unperfumed shampoo formulation of Table 7 under gentle shaking.

Example 10

Preparation of a Structured Shower Gel Comprising the Invention's Composition

TABLE 8

Composition of the milky shower gel formulation

| Ingredients | Amount (% wt) |
|---|---|
| WATER deionised | 49.350 |
| Tetrasodium EDTA[1] | 0.050 |
| Acrylates Copolymer[2] | 6.000 |
| Sodium C12-C15 Pareth Sulfate[3] | 35.000 |
| Sodium Hydroxide 20% aqueous solution | 1.000 |
| Cocamidopropyl Betaine[4] | 8.000 |
| Methylchloroisothiazolinone and Methylisothiazolinone[5] | 0.100 |
| Citric Acid (40%) | 0.500 |

[6]EDETA B POWDER; trademark and origin: BASF
[7]CARBOPOL AQUA SF-1 POLYMER; trademark and origin: NOVEON
[8]ZETESOL AO 328 U; trademark and origin: ZSCHIMMER & SCHWARZ
[9]TEGO-BETAIN F 50; trademark and origin: GOLDSCHMIDT
[10]KATHON CG; tradeark and origin: ROHM & HASS The transparent shower gel was prepared by adding 0.5 to 1.5% by weight, relative to the total weight of the shower gel, of the invention's composition of example 2 into the unperfumed shower gel formulation of Table 8 under gentle shaking.

Example 11

Preparation of a Eau De Toilette Comprising the Invention's Compound

The eau de toilette was prepared by adding 5 to 20% by weight, relative to the total weight of the eau de toilette, of the invention's composition of example 2 into ethanol under gentle shaking.

The invention claimed is:
1. A method to confer, enhance, improve, or modify the odor properties of a perfuming composition or of a perfumed article, with odor notes that are fruity-lactonic, tropical fruits, mango, slight passionfruit, with a pineapple undertone but not floral-jasmonic odor notes, which method comprises adding to said composition or article an effective amount of at least a compound of formula

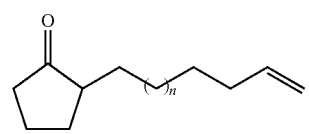

(I)

in a form of any one of its stereoisomers or a mixture thereof, and wherein n represents 1; wherein the compound of formula (I) possesses odor notes that are fruity-lactonic, tropical fruits, mango, slight passionfruit, with a pineapple undertone and lacks floral-jasmonic odor notes.

* * * * *